United States Patent [19]

Morganti

[11] Patent Number: 4,834,734

[45] Date of Patent: May 30, 1989

[54] INSOLUBLE COLLAGEN SUPPORT MATRIX CONTAINING RELEASEABLE SOLUBLE COLLAGEN AND METHOD OF MAKING THE SAME

[76] Inventor: Pierfrancesco Morganti, 49 Via Montoggio, 00168 Rome, Italy

[21] Appl. No.: 37,829

[22] Filed: Apr. 13, 1987

[51] Int. Cl.$^4$ ...................... A61F 13/00; A61F 13/16
[52] U.S. Cl. .................................... 604/368; 604/304
[58] Field of Search ........................ 128/DIG. 8, 156; 604/368, 304, 305; 514/801, 844, 847; 424/443, 445, 488; 530/356; 106/124

[56] References Cited

U.S. PATENT DOCUMENTS

| | | | |
|---|---|---|---|
| 3,823,212 | 7/1974 | Chvapil | 128/DIG. 8 |
| 3,991,184 | 11/1976 | Kludas et al. | 514/801 |
| 4,131,650 | 12/1978 | Braümer et al. | 128/DIG. 8 |
| 4,295,894 | 10/1981 | Cioca et al. | 530/356 |
| 4,320,201 | 3/1982 | Berg et al. | 604/280 |
| 4,374,121 | 2/1983 | Cioca | 514/179 |
| 4,389,487 | 6/1983 | Ries | 128/DIG. 8 |
| 4,412,947 | 11/1983 | Cioca | 530/356 |
| 4,451,397 | 5/1984 | Huc et al. | 128/DIG. 8 |
| 4,585,797 | 4/1986 | Cioca | 604/304 |
| 4,703,108 | 10/1987 | Silver et al. | 128/DIG. 8 |

FOREIGN PATENT DOCUMENTS

| | | | |
|---|---|---|---|
| 2462221 | 5/1976 | Fed. Rep. of Germany | 424/124 |
| 2067573 | 7/1981 | United Kingdom | 530/356 |

OTHER PUBLICATIONS

Johnson, "Proteins in Cosmetics and Toiletries", Drug Cosmet. Indust., vol. 126, pp. 36–39, 139, Jun. 1980.
Todd et al., "Soluble Collagen–New Protein for Cosmetics", Drug Cosmet. Indust., vol. 117, pp. 50–56, 134–138, Oct. 1975.

Primary Examiner—John D. Yasko
Assistant Examiner—Sharon Rose
Attorney, Agent, or Firm—Marshall & Melhorn

[57] ABSTRACT

A spongy and felt-like support material, consisting of an insoluble collagen matrix containing releaseable soluble collagen, is used as:

(1) a cosmetic carrier for the application of moisturizing collagen to the skin, or
(2) a pharmaceutical carrier for the application of topically efficacious therapeutics.

8 Claims, No Drawings

INSOLUBLE COLLAGEN SUPPORT MATRIX CONTAINING RELEASEABLE SOLUBLE COLLAGEN AND METHOD OF MAKING THE SAME

The present invention relates to a spongy, felt-like support matrix made of reticulated, insoluble natural animal collagen, the support containing releasable soluble collagen. The support matrix and soluble collagen are very effective topical dressings for the skin including dressings for dry skin, skin burns and skin wounds.

BACKGROUND OF THE INVENTION

Collagen is a well known constituent of white fibrous tissue in animals. It is found in bone, cartilage and tendons, but particularly in cutaneous and subcutaneous connective tissue.

Methods for extracting collagen from tissue are well known. The preparation of an insoluble felt like collagen matrix is known as shown in U.S. Pat. No. 3,823,212.

While collagen support materials with a spongy or felt-like structure are already known, see U.S. Pat. No. 3,823,212, their denaturation temperatures are too low, or they cannot release natural soluble collagen (either in aqueous solution or on contact with the skin) since they are produced using highly reticulated chemical binding substances. When treated with these chemical binding substances, such as timing agents, natural collagen is irreversibly reticulated so as to bind any natural soluble collagen almost completely. The word reticulated used herein, as seen in the prior art, including U.S. Pat. No. 3,823,212 refers to the net-like, crossed-fiber network of the felt-like sponge. Furthermore, the presence of these binding substances, or of preservative substances, works against the main cosmetic purpose of treatment of dry skin. They may, in fact, be quite damaging to the skin itself.

Attempts have previously been made to solve this problem by using natural soluble collagen in oil/water emulsions, in aqueous or glycol solutions, or in other chemico-physical forms to be used either directly on the skin or by application on a reticulated collagen support at the moment of use. HOwever these products suffer from the severe disadvantage that collagen in solutions or emulsions has an extremely brief and often indeterminant life cycle due to its rapid denaturation. Therefore, the use of preservatives is required and efficacy is even then not reliable.

The following publications describe the techniques of preparing an insoluble collagen felt-like matrix:

K. H. Stenzel, T. Miyata, A. L. Rubin, Collagen as biomaterial *Ann. Rev. Blophys. Bioeng.*, 3,231–253 (1974); U.S.A. Pat. No. 3,823,212; German patent No. 2625289;

A. Berg, H. Lindner, Schutz-proteine in der Kosmetik *Parf. & Kosm.*, 60, 74–78 (1979); U.S. Pat. No. 4,193,813;

A. Berg, H. Dieringer, Collagen mask—Cosmetic Application & Analytical Control; *Atti Congresso Naz. SICC.*, Milan 24–25 Nov 1983;

M. Chvapil, Z. Eckmayer, Role of proteins in cosmetics, *Int. Journal of Cos. Science*, 7, 41–49 (1985)

In the prior art, there is not cosmetic product based upon soluble collagen (such as emulsions, or aqueous or glycol solutions) which offers the guaranteed availability of a high concentration of natural soluble collagen, with its inherent chemico-physical behavior allowing complexation with other components and simultaneously having such stability.

Furthermore, the possibility of incorporating into the collagen matrix other cosmetically or pharmacologically active substances gives rise to the possibility of a product for local application to the skin which, in addition to its moisturizing effects, may also show therapeutic activity.

OBJECTS OF THE INVENTION

It is an object of the present invention to provide a spongy support matrix of insoluble, reticulated collagen containing releaseable soluble collagen.

Therefore, one object of the present invention is a biologically active support matrix consisting of natural animal collagen wherein said matrix contains water-insoluble reticulated collagen as well as a quantity of 4% to 50% by weight of natural, water-soluble non-reticulated collagen, with a denaturation temperature higher than 37° C., which may be dissolved in the presence of water.

It is an object of the present invention to provide an insoluble collagen support matrix material natural and soluble collagen combined with the natural insoluble collagen (treated with no chemical reticulating agents) to obtain a final product which, when moistened or placed in contact with the skin, releases desirable natural soluble collagen while the insoluble collagen fibers form a uniform, moist, semi-occlusive supporting layer.

It is an object to provide an insoluble collagen support matrix that releases natural soluble collagen on the skin and the moisturizing process is enhanced. This has been shown in the prior art including: Todd, R.D. Soluble collagen: new protein for cosmetics., Drug Cosmet. Indust. Vol. 117 50–2. 56, 134–38 (1975) and Johnsen, V.L., Proteins in cosmetics and toiletries, Drug Cosmet. Indust. Vol. 126 36–9, 126 (1980).

Another object of the present invention is a process for the preparation of said support, comprising the following steps:

dissolving in distilled and/or sterilized water at room temperature a quantity of enriched natural soluble collagen prepared using known methods from biological tissue of young mammals, so as to obtain a solution with a concentration of from 5% to 40% by weight of collagen which does not degrade at temperatures below 37° C.

addition of a quantity of insoluble collagen to the solution in a proportion ranging from 0.5:1.0 to 1.0:0.5 with respect to the soluble collagen, while stirring to obtain a homogeneous mixture.

With continued stirring of said mixture rapid cooling down to a temperature between 0° C. and and −5° C., thus obtaining a pourable mixture to be placed in forms for lyophilization. lyophilization in said forms.

These and other objects will be apparent from the specification that follows and the appended claims.

SUMMARY OF THE INVENTION

The present invention provides an active insoluble collagen support matrix which is spongy or felt-like in appearance comprising a natural animal insoluble collagen matrix, wherein said matrix comprises a water-insoluble reticulated collagen about 4% to 50% by weight of natural, water-soluble non-reticulated collagen, the matrix having a denaturation temperature higher than 37° C. which may be dissolved in the presence of water.

The present invention also provides a process for the preparation of the support matrix according to claim 1, comprising the steps of:

dissolving in distilled and/or sterilized water at room temperature a quantity of enriched natural soluble collagen prepared suing known methods from biological tissue of young mammals, so as to obtain a solution with a concentration of from about 5% to 40% by weight of collagen which does not degrade at temperatures below about 37° C.

addition of a quantity of insoluble collagen to the solution in a proportion ranging from about 0.5:1 to 1:0.5 with respect to the soluble collagen, stirring to obtain a homogeneous mixture;

during continued stirring of said mixture, rapid cooling down to a temperature between about 0° C. and −5° C., so as to obtain a pourable mixture to be placed in forms for lyophilization lyophilization in said forms.

DETAILED DESCRIPTION OF THE INVENTION

It should be noted that the denaturation temperature of collagen depends on the starting material used for extraction of the collagen itself. The starting material should therefore be selected on the basis of known criteria so that the collagen has a denaturation temperature higher than about 37° C. when it is prepared, preferable between about 39° C. and 45° C. Collagen denaturation, however, does not depend on temperature alone but on other factors as well, such as the presence of chemical substances.

Therefore, according to the present invention, the stable storage capacity of the soluble collagen does not depend directly on the natural denaturation temperature established by the choice of starting material as mentioned above, but on the characteristics of the production process and the material so obtained, unlike similar known products.

The preferred starting material for the soluble collagen is fresh tissue from young mammals such as calves, pigs, guenea pigs and rats, ideally in enriched solutions.

According to the invention, said mammalian source is dissolved in cold distilled and/or sterilized water, so as to achieve a solution with a concentration of active substance between about 5% and 40% by weight with respect to the total solution. The solution is checked analytically to ensure that its denaturation temperature is not below about 37° C. or 38° C.

The novel product can be used for the incorporation of cosmetically or pharmacologically active substances, with the advantage that the support may be stored with none of the denaturation of degradation problems encountered with similar known products.

Also, the support matrix according to this invention may be prepared in various forms (such as spheres, cylinders of sheets) which may, due to its soft spongy or felt-like structure, be cut into the size and thickness desired.

Also, the presence of natural insoluble collagen, while not an active substance in itself, endows the support matrix with considerable firmness, facilitating handling during production and packaging as well as easy application to, and removal from, the skin.

The product may be used for cosmetic or pharmacologic purposes by bringing suitable forms (eg: sheets) into contact with the desired area of the skin surface. The natural moisture of the skin then dissolves the soluble collagen and any other active substances, which can then exert their effects upon the skin. The products and methods of the present invention help to enhance the appearance of the skin.

As is known in the art the cosmetic and pharmacologic materials include gelatin; the amino acids such as glycine, lycine and 1-cystine,; clays, calcium carbonate, pigments, zinc oxide, and substances disclosed in U.S. Pat. No. 3,823,212 such as blood clotting inhibitors, blood clotting promotors, analgesic agents and anitbiotics such as bacitracin, neomycin and tetracyclin.

The support matrix material, according to this invention, differs from previous collagen based materials in two ways:

First, it is charged with natural, soluble and stable collagen when it is packaged and it releases said collagen in high quantities upon contact with the skin. Second, since no preservatives or reticulating agents are used in the support material in this invention, there are none of the negative reactions which may ensue with similar previous products, such as irritation or rejection caused by trace residues of these preservatives or chemical binding substances.

An important advantage of the novel products and methods is that the support material may be stored in the dry state with no addition of preservatives. In fact, it may be sterilized with gamma radiation if suitably packaged. This sterilization is impossible with natural soluble collagen incorporated in emulsions or aqueous solutions. According to the invention, the natural soluble collagen in the support matrix remains stable without preservatives for long periods, even at high ambient room temperatures. This stability cannot be assured for products in aqueous solution.

The present invention produces from natural collagen (prepared using known methods), a biologically active support consisting of collagen which can release, both in aqueous solution and in contact with the skin, from about 0.5% to 50% of its weight in natural soluble animal collagen. Such a support must have a denaturation temperature no lower than about 37° C. This support is a new product and it has cosmetological activity because the soluble collagen is recognized as being useful in the art.

Hence, this invention provides a support matrix product for cosmetic or pharmaceutical use consisting of insoluble collagen and soluble collagen which product is partially naturally reticulated and insoluble and partially water soluble. When brought into contact with the skin, this support matrix product has the property of transferring back into the skin a considerable quantity of water from the insensible perspiration of the skin. This support matrix product is therefore suitable for use in the treatment of dry skin and for facilitating the penetration of active substances into the skin.

What is claimed is:

1. A process for the preparation of a support sponge matrix containing releasable soluble collagen, the process consisting essentially of the steps of:
   (a) dissolving, in water at room temperature, a quantity of enriched natural soluble collagen prepared using known methods from biological tissues of young mammals, so as to obtain a solution having a concentration from about 5% to 40% by weight of collagen which does not degrade at temperatures below about 37° C.;

(b) adding a quantity of insoluble collagen to the solution in a proportion by weight ranging from about 0.5:1 to 1:0.5 with respect to the soluble collagen of step a;

(c) stirring to obtain a homogeneous mixture;

(d) during the continued stirring of said mixture, rapidly cooling the mixture to a temperature from about 0° C to −5° C., so as to obtain a pourable mixture to be placed in forms for lyophilization;

(e) lyophilizing the mixture in said forms; and (f) optionally, adding cosmetically or pharmacologically active substances to the mixture during any of the steps (a) through (c), inclusive.

2. A process according to claim 1, wherein the soluble collagen solution is filtered to remove any impurities before the addition of the insoluble collagen.

3. A process as defined in claim 1, wherein the proportion of insoluble collagen to soluble collagen is about 1:1.

4. A support sponge matrix containing releasable soluble collagen prepared by the process defined in claim 1.

5. A support sponge matrix containing releasable soluble collagen, comprising a natural uncrosslinked insoluble collagen matrix, and a soluble natural releasable collagen within the matrix, wherein the weight ratio of insoluble collagen to soluble collagen is about 0.5:1 to 1:0.5, the soluble collagen is soluble in water, and having a denaturation temperature from about 37° C. to 45° C.

6. A support sponge matrix containing releasable soluble collagen as defined in claim 5, wherein the weight ratio of natural soluble collagen to soluble collagen is about 1:1.1

7. A support sponge matrix containing releasable soluble collagen, comprising:

(a) an uncrosslinked natural animal insoluble collagen matrix; and (b) about 4% to about 50% by weight of natural water soluble releasable collagen; wherein the support sponge matrix containing releasable soluble collagen has a denaturation temperature greater than 37° C.

8. The support sponge matrix containing releasable soluble collagen, according to claim 7, further comprising cosmetically or pharmacologically active substances.

* * * * *

UNITED STATES PATENT AND TRADEMARK OFFICE
CERTIFICATE OF CORRECTION

PATENT NO. : 4,834,734
DATED : May 30, 1989
INVENTOR(S) : Pierfrancesco Morganti It is certified that error appears in the above-identified patent and that said Letters Patent is hereby corrected as shown below:

In column 1, line 65 of the Patent, change "not" to --no--.

In column 2, line 39 of the Patent, delete second "126" and insert --136--.

Signed and Sealed this

Twenty-first Day of August, 1990

Attest:

HARRY F. MANBECK, JR.

Attesting Officer     Commissioner of Patents and Trademarks